(12) United States Patent
Wight et al.

(10) Patent No.: US 12,318,075 B2
(45) Date of Patent: Jun. 3, 2025

(54) FLUID SAMPLE COLLECTION CONTAINER WITH REMOVABLE TUBE HOLDER

(71) Applicant: Becton, Dickinson and Company, Franklin Lakes, NJ (US)

(72) Inventors: David Colie Wight, West Orange, NJ (US); Michael Baker, Oradell, NJ (US); Daniel Feltyberger, Sparta, NJ (US); Elizabeth Stayduhar, Charlestown, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 182 days.

(21) Appl. No.: 18/013,061

(22) PCT Filed: Jun. 30, 2021

(86) PCT No.: PCT/US2021/039875
§ 371 (c)(1),
(2) Date: Dec. 27, 2022

(87) PCT Pub. No.: WO2022/006264
PCT Pub. Date: Jan. 6, 2022

(65) Prior Publication Data
US 2023/0240669 A1 Aug. 3, 2023

Related U.S. Application Data

(60) Provisional application No. 63/047,077, filed on Jul. 1, 2020.

(51) Int. Cl.
*G01N 1/10* (2006.01)
*A61B 10/00* (2006.01)

(52) U.S. Cl.
CPC ........ *A61B 10/0096* (2013.01); *A61B 10/007* (2013.01)

(58) Field of Classification Search
CPC .............. A61B 10/007; A61B 10/0045; A61B 10/0096; G01N 1/10; G01N 2001/10
See application file for complete search history.

(56) References Cited

U.S. PATENT DOCUMENTS

| 4,020,970 A | 5/1977 | Koscik et al. |
| 4,300,404 A | 11/1981 | Mehl et al. |

(Continued)

FOREIGN PATENT DOCUMENTS

| JP | S5279149 | 7/1977 |
| JP | S5664639 | 6/1981 |

(Continued)

*Primary Examiner* — Alexander A Mercado
(74) *Attorney, Agent, or Firm* — The Webb Law Firm (57) ABSTRACT

A container assembly including a collection container and a container lid couplable to the collection container. A specimen collection tube holder having an elongated receptacle formed therein is provided, the elongated receptacle being configured to receive a specimen collection tube. The specimen collection tube holder is removably couplable to a central portion of the container lid such that at least a portion of the elongated receptacle extends into the chamber of the collection container when the container lid is coupled to the collection container and the specimen collection tube holder is coupled to the container lid.

15 Claims, 7 Drawing Sheets

(56) References Cited

U.S. PATENT DOCUMENTS

| | | | |
|---|---|---|---|
| 4,927,605 A * | 5/1990 | Dorn | A61B 10/007 |
| | | | 422/68.1 |
| 5,312,009 A | 5/1994 | Ratajczak et al. | |
| 5,595,187 A * | 1/1997 | Davis | B01L 3/502 |
| | | | 600/584 |
| 5,928,200 A * | 7/1999 | Thorne | A61B 5/15003 |
| | | | 604/263 |
| 6,054,009 A | 4/2000 | Cote et al. | |
| 6,921,395 B2 | 7/2005 | Carano et al. | |
| 7,517,495 B2 | 4/2009 | Wu et al. | |
| 9,775,550 B2 | 10/2017 | Schaffer | |
| 9,931,102 B1 * | 4/2018 | Studer | A61B 10/007 |
| 10,493,447 B2 | 12/2019 | Mangiafico et al. | |
| 2003/0036742 A1 | 2/2003 | Carano et al. | |
| 2003/0053938 A1 * | 3/2003 | Szeles | A61B 10/007 |
| | | | 600/583 |
| 2005/0032239 A1 | 2/2005 | Katz | |
| 2005/0048670 A1 | 3/2005 | Wu et al. | |
| 2013/0175266 A1 | 7/2013 | Ellis | |
| 2014/0213934 A1 * | 7/2014 | Ellis | A61B 10/0096 |
| | | | 600/573 |
| 2016/0054202 A1 * | 2/2016 | Yong | A61B 10/0096 |
| | | | 73/864.63 |
| 2018/0325497 A1 * | 11/2018 | Katz | A61B 10/007 |

FOREIGN PATENT DOCUMENTS

| | | |
|---|---|---|
| JP | H07275323 A | 10/1995 |
| JP | 2003139780 A | 5/2003 |
| JP | 201834840 A | 3/2018 |

* cited by examiner

FLUID SAMPLE COLLECTION CONTAINER WITH REMOVABLE TUBE HOLDER

CROSS-REFERENCE TO RELATED APPLICATIONS

This application is the United State, nation of International Application No. PCT/US2021/039875 filed Jun. 30, 2021, and claims priority to U.S. Provisional Application Ser. No. 63/047,077, entitled "Fluid Sample Collection Container with Removable Tube Holder", filed Jul. 1, 2020, the entire disclosures of which are hereby incorporated by reference in their entirety.

BACKGROUND

Field of the Disclosure

The present disclosure relates generally to a container assembly for collecting a fluid specimen. More particularly, the present disclosure relates to a container assembly including a removable specimen collection tube holder.

Description of the Related Art

To conduct laboratory testing on biological fluid samples such as urine, it is necessary to provide a container for collecting the fluid sample. These collection containers typically include a cup-shaped container with a removable lid. Once a fluid sample has been collected in the container, the lid is reapplied. The collection container may then be transported to a laboratory or other testing facility where a sample of the collected specimen is extracted for test purposes.

To simplify the sample extraction process, prior collection containers have used lids which not only cover and seal the collection container, but also provide for the use of an extraction device which permits the extraction of a sample of the fluid specimen. Such lids may include a receptable or cavity which supports a tube extending within the cavity to the lower end of the cup-shaped container in fluid communication with the specimen contained within the container. The tube or the lid may include an integrated elongated receptacle housing a cannula and needle so that an air-evacuated collection device (e.g., a specimen collection tube) may be attached thereto to draw a portion of the collected sample thereinto without the need for removal of the lid. In such configurations, the sample can be removed without spilling or contaminating the sample and/or cavity area. Subsequent samples may be drawn from the collection container by using a plurality of collection tubes.

However, in prior collection containers, the needle is provided within the elongated receptacle as part of a finger grip luer adapter (FGLA) that is non-removably integrated into the container lid. Thus, when the user has completed all sample collection(s) and wishes to dispose of the container assembly, the entire removable lid must be disposed of in an appropriate sharps container or sharps biohazard container. Due to their large volume, removable lids will quickly fill the sharps container, necessitating frequent service by a qualified disposal firm to safely handle the sharps and/or biohazard waste. As such disposal services are far more expensive than conventional waste disposal services, health care providers generally seek to minimize the accumulated volume of sharps and/or biohazard waste.

Additionally, due to the FGLA being integrated into the lid, the patient and/or healthcare worker may be more at risk of needle-stick injuries during sample collection, transport, and/or disposal.

SUMMARY

In view of the foregoing, there exists a need for a fluid sample collection container having a reduced volume of sharps waste and which protects users and/or healthcare workers from potential needle-stick injuries.

In accordance with an embodiment of the present invention, a container assembly for collecting a fluid specimen includes a collection container defining a chamber for receiving the fluid specimen and a container lid couplable to an open end of the collection container to at least partially close the open end thereof. The container assembly also includes a container lid couplable to an open end of the collection container to at least partially close the open end thereof, and a specimen collection tube holder having an elongated receptacle formed therein, the elongated receptacle configured to receive a specimen collection tube, in which the specimen collection tube holder is removably couplable to a central portion of the container lid such that at least a portion of the elongated receptacle extends into the chamber of the collection container when the container lid is coupled to the collection container and the specimen collection tube holder is coupled to the container lid.

In certain configurations, the central portion of container lid includes an opening sized and configured to receive the elongated receptacle of the specimen collection tube holder. The container lid may also include at least one retaining member, wherein the at least one retaining member is configured to secure the specimen collection tube holder to the container lid. The specimen collection tube holder may include at least one flange arranged peripherally to a receiving cavity of the elongated receptacle.

Optionally, the at least one flange may be configured to engage the at least one retaining member. The at least one retaining member may include a slot, and the at least one flange is may be configured to engage the slot when the specimen collection tube holder is coupled to the container lid. The specimen collection tube holder may also include a pair of opposed, upwardly extending wings arranged peripherally to the receiving cavity of the elongated receptacle.

The specimen collection tube holder is couplable to the container lid by a quarter-turn rotation in a first direction and decouplable from the container lid by a quarter-turn rotation in a second direction. Optionally, the specimen collection tube holder may be coupled to the container lid by a perforated seam. The specimen collection tube holder may further include a pull tab. In certain configurations, an upward pulling force on the pull tab tears the perforated seam and separates the specimen collection tube holder from the container lid.

In accordance with another embodiment of the present invention, a container lid assembly for use with a container assembly for collecting a fluid specimen includes a container lid configured to be couplable to an open end of a collection container, and a specimen collection tube holder having an elongated receptacle formed therein. The elongated receptacle is configured to receive a specimen collection tube and the specimen collection tube holder is removably couplable to a central portion of the container lid.

In certain configurations, the container lid further includes at least one retaining member, that is configured to secure the specimen collection tube holder to the container lid. The specimen collection tube holder may include at least one flange arranged peripherally to a receiving cavity of the elongated receptacle. The flange may be configured to engage a slot formed in the at least one retaining member when the specimen collection tube holder is coupled to the container lid.

In other configurations, the specimen collection tube holder further includes a pair of opposed, upwardly extending wings arranged peripherally to the receiving cavity of the elongated receptacle. The specimen collection tube holder may also be coupled to the container lid by a perforated seam. Optionally, the specimen collection tube holder may further include a pull tab, and an upward pulling force on the pull tab may tear the perforated seam and separate the specimen collection tube holder from the container lid.

In accordance with yet another embodiment of the present invention, a method of forming a container assembly for collecting a fluid specimen includes the steps of providing a collection container defining a chamber for receiving the fluid specimen, providing a container lid couplable to the collection container, and providing a specimen collection tube holder separate from the container lid. The specimen collection tube holder may include an elongated receptacle formed therein configured to receive a specimen collection tube. The method may also include the step of coupling the specimen collection tube holder to a central portion of the container lid such that at least a portion of the elongated receptacle extends into the chamber of the collection container when the container lid is coupled to the collection container and the specimen collection tube holder is coupled to the container lid.

The method may also include the steps of decoupling the specimen collection tube holder from the container lid when a specimen collection task is completed, and disposing of the specimen collection tube holder separately from the container lid and the collection container.

Further details and advantages of the present disclosure will be understood from the following detailed description read in conjunction with the accompanying drawings.

DESCRIPTION OF THE INVENTION

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For the purposes of the description hereinafter, the terms "upper", "lower", "right", "left", "vertical", "horizontal", "top", "bottom", "lateral", "longitudinal", and derivatives thereof shall relate to the invention as it is oriented in the drawings. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

Figure 1:
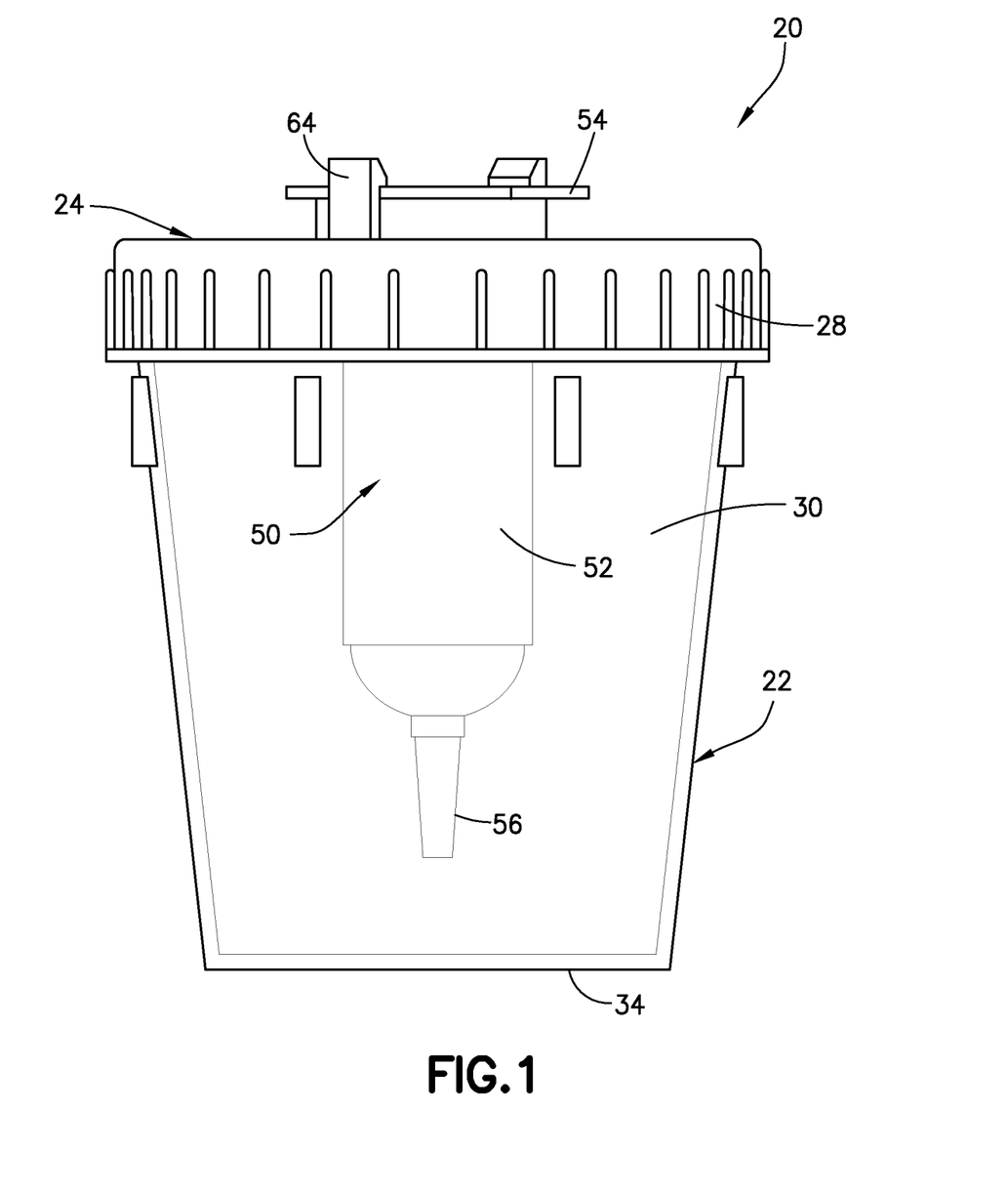
FIG. 1 is a side view of a fluid sample collection container assembly in accordance with an aspect of the present disclosure.
Figure 2:
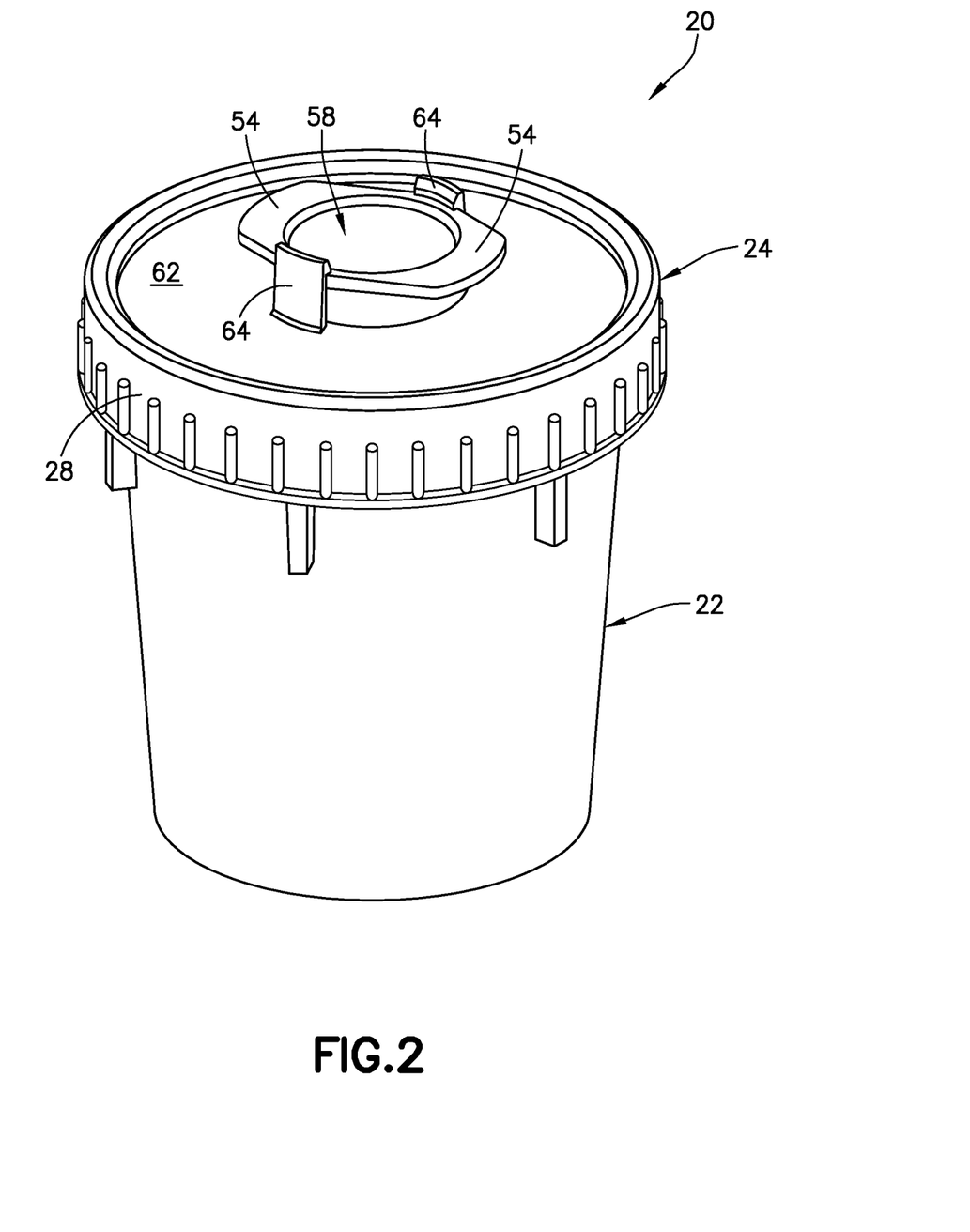
FIG. 2 is a top perspective view of the fluid sample collection container assembly of FIG. 1.

Referring to FIGS. 1 and 2, a fluid sample collection container assembly 20 in accordance with an aspect of the present disclosure is shown. Fluid sample collection container assembly 20 includes a collection container 22 and a container lid 24. An exemplary collection container assembly 20 in accordance with the present disclosure may be used to safely collect a fluid specimen (e.g., urine), transport the fluid specimen, and draw a sample of the fluid specimen.

In one embodiment, collection container 22 and container lid 24 may be formed from any conventional material such as, e.g., a polymeric resin. Polymeric resins are well known in the art and include, for example, polyethylene, polycarbonate, polystyrene, and similar polymeric resinous materials. However, it is to be understood that collection container 22 and/or container lid 24 may be formed of other appropriate materials, and may be formed of different materials.

Collection container 22 generally includes a sidewall 30 extending between a first, open end (not shown) and a second, closed end 34. Sidewall 30 defines an interior chamber for receiving a fluid specimen such as, e.g., urine. In one embodiment, sidewall 30 of collection container 22 comprises a slightly tapering, tubular vessel having continuous, tapered sidewalls 30. In one embodiment, the collection chamber of container 22 is suitable for holding biologically hazardous materials. In one embodiment, sidewall 30 of collection container 22 may include at least one fill level indicator which identifies a fluid level of a collected fluid specimen.

Figure 3:
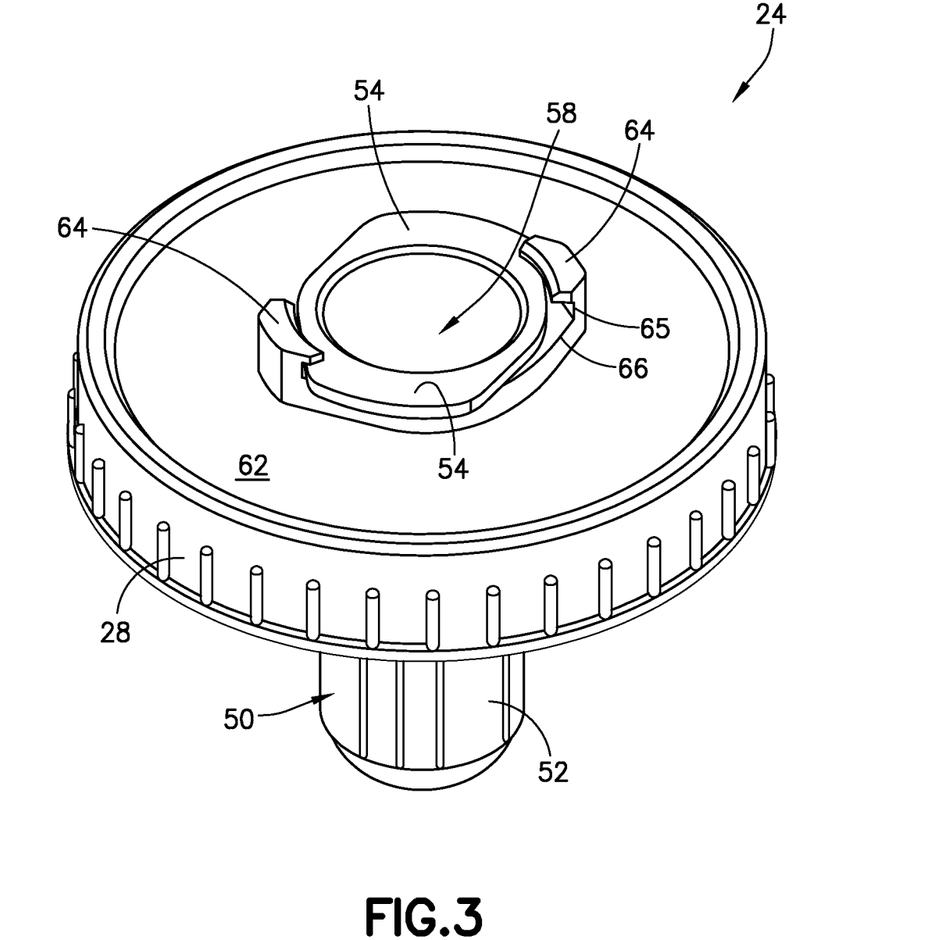
FIG. 3 is a top perspective view of a container lid assembly of the fluid sample collection container assembly of FIG. 1.
Figure 4:
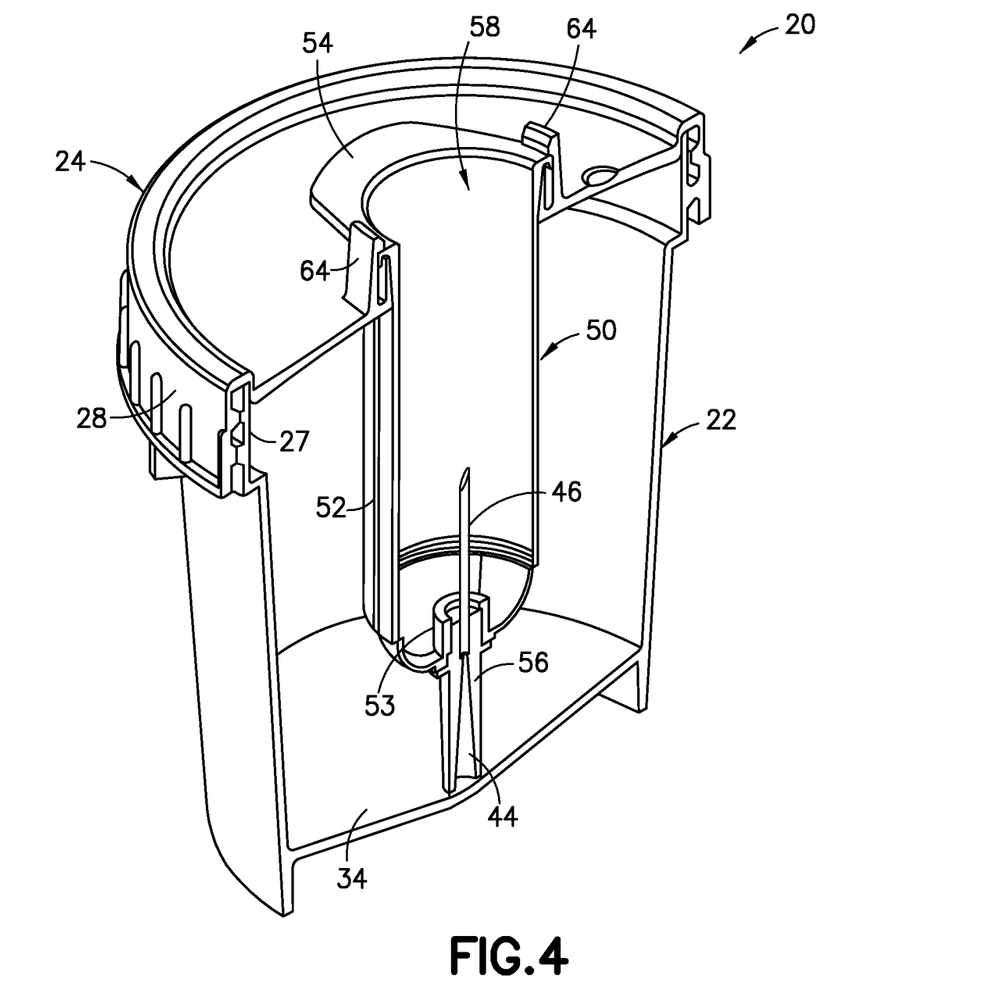
FIG. 4 is a cross-sectional perspective view of the fluid sample collection container assembly of FIG. 1.

As shown in FIGS. 1-4, container lid 24 generally includes a flange 28 extending around its outer rim, with flange 28 being sized to provide a tight fit upon the collection container 22 when container lid 24 is placed over the first, open end of collection container 22. As shown in FIG. 4, flange 28 includes an inner surface which includes a means or mechanism for sealingly engaging container lid 24 with a corresponding connection interface 27 of the collection container 22. In one embodiment, flange 28 includes an interior threaded portion, thereby enabling container lid 24 to be threadingly connectable to a corresponding exterior threaded portion of the connection interface 27 of the collection container 22. In other embodiments, the sealing portion of container lid 24 may include a snap fit mechanism, a ball detent, an interference fit mechanism, locking tabs, a spring loaded locking mechanism, a latch, or other similar mechanism to sealingly engage container lid 24 to collection container 22, thereby substantially preventing a fluid specimen contained within collection container 22 and container lid 24 from leaking out, while also preventing contaminants from entering. In other embodiments, the engagement between container lid 24 and collection container 22 may be configured to allow the passage of air into and out of the fluid sample collection container assembly 20, while substantially preventing the egress of fluid therefrom. In this way, the formation of a vacuum within the fluid sample collection container assembly 20 may be substantially avoided.

In one embodiment, container lid 24 includes a central portion 62. Extending upward from central portion 62 are a pair of retaining members 64. As shown in FIG. 3, each retaining member 64 includes a slot 65. Additionally, in one embodiment, a raised portion 66 may extend circumferentially around an opening (not shown) formed in central portion 62 of container lid 24. In one embodiment, the retaining members 64 and raised portion 66 are integrally formed with the central portion 62 of the container lid 24. In another embodiment, at least one of the retaining members 64 and the raised portion 66 may be formed separately from the central portion 62 and are affixed to the central portion 62 by any appropriate method. Furthermore, while two retaining members 64 are illustrated in FIGS. 2-4, it is to be understood that more or fewer retaining members 64 may be utilized in accordance with other embodiments of the disclosure.

Referring still to FIGS. 1-4, the fluid sample collection container assembly 20 further includes a specimen collection tube holder 50, with specimen collection tube holder 50 being removably coupled to the container lid 24. Specimen collection tube holder 50 includes an elongate receptacle 52, wherein elongate receptacle 52 is configured to extend into collection container 22 and towards the second, closed end 34 of collection container 22 when the container lid 24 is coupled to the collection container 22 and the specimen collection tube holder 50 is coupled to the container lid 24.

Specimen collection tube holder 50 includes a receiving cavity 58 defined therein, with a pair of tube holder flanges 54 disposed radially outside of an open end of the receiving cavity 58. An opposing lower end portion 56 is defined below the elongate receptacle 52. In one embodiment, receiving cavity 58 is sized and shaped to receive a specimen collection tube such as, e.g., an evacuated tube (not shown). As shown in FIG. 4, in one embodiment, lower end portion 56 is configured as a cannula coupled to (or integrated with) a connection interface 53 formed at a lower portion of specimen collection tube holder 50. In one embodiment, lower end portion 56 is threadingly engaged with the connection interface 53. The lower end portion 56 includes a needle 46 which extends into elongate receptacle 52, wherein the needle 46 is configured to pierce a stopper of the specimen collection tube when the specimen collection tube is inserted into the receiving cavity 58. In this way, a fluid specimen within collection container 22 can be transferred to the specimen collection tube via a through-hole 44 formed within lower end portion 56 and the needle 46, thus eliminating a need to remove the container lid 24 to collect a specimen.

Prior to use of the fluid sample collection container assembly 20, the specimen collection tube holder 50 is secured to the container lid 24. As shown in FIG. 3, the tube holder flanges 54 are sized and positioned so as to at least partially engage the slots 65 of the retaining members 64. Thus, with a predetermined amount of rotation (e.g., a quarter-turn clockwise rotation) of the specimen collection tube holder 50, the specimen collection tube holder 50 can be securely coupled to the container lid 24 via the interface between the tube holder flanges 54 and the retaining members 64.

Conversely, the specimen collection tube holder 50 can be manually removed from the container lid 24 by way of an opposite rotation of the tube holder flanges 54. For example, a user may rotate the specimen collection tube holder 50 in a counterclockwise direction, thereby releasing the tube holder flanges 54 from their engagement with slots 65 of the retaining members 64. The specimen collection tube holder 50 may then be separated from the container lid 24. The tube holder flanges 54 may be sized to extend at least partially beyond the raised portion 66 of container lid 24, thereby providing the user with at least one surface upon which to lift the specimen collection tube holder 50 away from the container lid 24.

While a quarter-turn connection/disconnection is disclosed herein, it is to be understood that other types of connection interfaces between the specimen collection tube holder 50 and the container lid 24 are also possible, such as, e.g., a bayonet connection, a snap-fit connection, etc.

After use of the fluid sample collection container assembly 20, the user (e.g., a healthcare worker) may separate the specimen collection tube holder 50 from the container lid 24, disposing of only the specimen collection tube holder 50 in a sharps or sharps biohazard container, while disposing of remainder of the container lid 24 and the collection container 22 in a general waste container. In this way, the volume of waste disposed of in a sharps or sharps biohazard container is greatly reduced. Furthermore, when disposing of the various components of the fluid sample collection container assembly 20, the user need not touch any portion of the specimen collection tube holder 50, the container lid 24, and/or the collection container 22 which came into contact with the fluid specimen (e.g., urine).

In one embodiment, specimen collection tube holder 50 is a conventional specimen collection tube holder such as, e.g., a BD Vacutainer® one-use holder. Accordingly, many healthcare workers will be accustomed to handling the specimen collection tube holder 50 and, thus, will understand that it is to be disposed of in an appropriate sharps container after use. Furthermore, use of a conventional specimen collection tube holder allows for a reduction in the overall size and material necessary to form the container lid 24, which may reduce equipment tooling and manufacturing cost. Additionally, because the convention specimen collection tube holder is produced at high volumes for various other uses, it may be more efficient and cost-effective to produce as compared to a container lid having an integrated tube holder.

Figure 5:
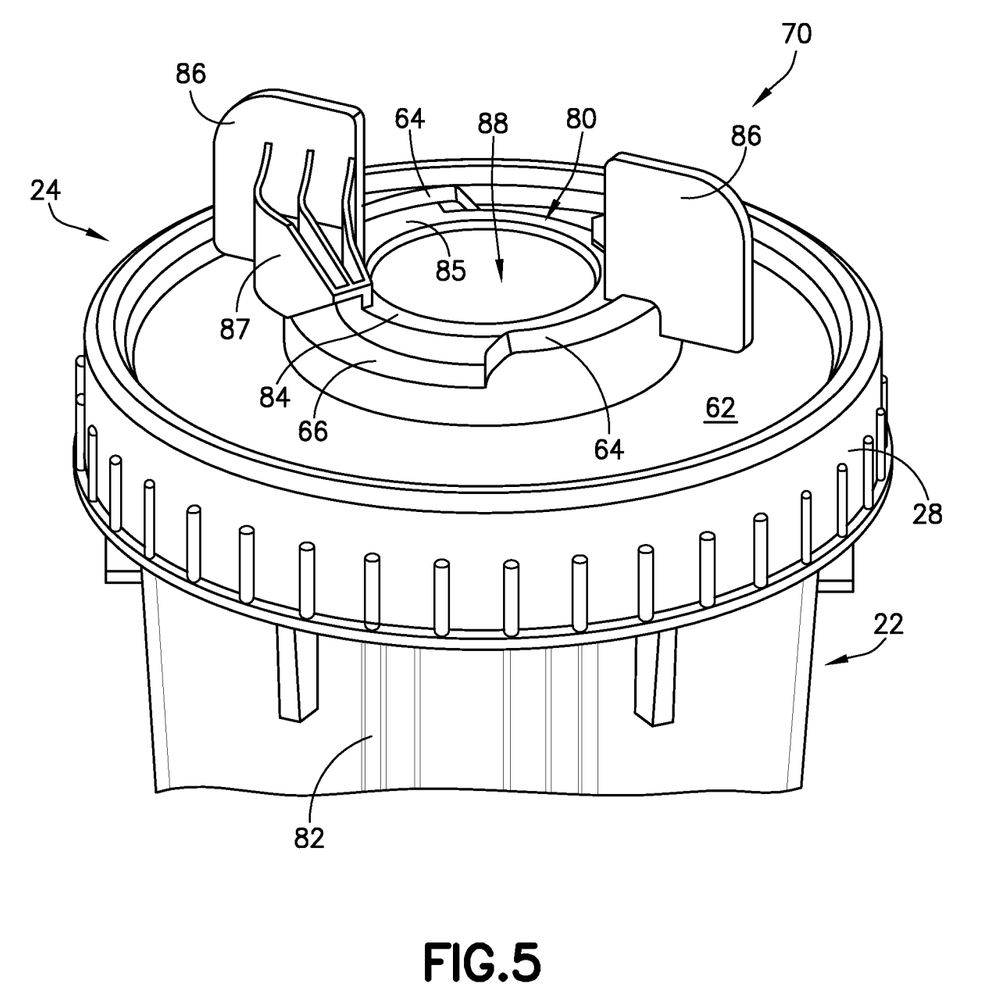
FIG. 5 is a top perspective view of a container lid for use with a fluid sample collection container assembly in accordance with another aspect of the disclosure.

Next, referring to FIG. 5, a fluid collection container assembly 70 in accordance with another aspect of the disclosure is shown. Components of fluid collection container assembly 70 equivalent to those of fluid collection container assembly 20 use common reference numbers and, thus, will not be reiterated herein.

Fluid sample collection container assembly 70 includes a specimen collection tube holder 80, with specimen collection tube holder 80 being removably coupled to the container lid 24. Specimen collection tube holder 80 includes an elongate receptacle 82, wherein elongate receptacle 82 is configured to extend into collection container 22 when the container lid 24 is coupled to the collection container 22 and the specimen collection tube holder 80 is coupled to the container lid 24.

Specimen collection tube holder 80 includes a receiving cavity 88 defined therein, with tube holder flanges 85 disposed radially outside of an open end of the receiving cavity 88. In one embodiment, receiving cavity 88 is sized and shaped to receive a specimen collection tube such as, e.g., an evacuated tube (not shown). While not shown, a needle is disposed within elongate receptacle 82, wherein the needle is configured to pierce a stopper of the specimen collection tube when the specimen collection tube is inserted into the receiving cavity 88. In this way, a fluid specimen within collection container 22 can be transferred to the specimen collection tube without the need to remove container lid 24.

Prior to use of the fluid sample collection container assembly 70, the specimen collection tube holder 80 is secured to the container lid 24. As shown in FIG. 5, the tube holder flanges 85 are sized and positioned so as to at least partially engage slots of the retaining members 64. Thus, with a predetermined amount of rotation (e.g., a quarter-turn clockwise rotation) of the specimen collection tube holder 80, the specimen collection tube holder 80 can be securely coupled to the container lid 24 via the interface between the tube holder flanges 85 and the retaining members 64.

Specimen collection tube holder 80 further includes a pair of opposed, upwardly extending wings 86, which provide for an ergonomic interface upon which the user may rotate the sample collection tube holder 80 for connection/disconnection from the container lid 24. Each wing 86 is coupled to a rim 84 of the sample collection tube holder 80, and each wing 86 further includes a bracing element 87, with bracing elements 87 reinforcing the wings 86 and maintaining the wings 86 in an upwardly-extending position when rotational force is applied thereto.

In addition to being secured to the container lid 24, the specimen collection tube holder 80 can also be manually removed from the container lid 24 by way of an opposite rotation of the tube holder flanges 85 by way of the wings 86. For example, a user may rotate the specimen collection tube holder 80 in a counterclockwise direction, thereby releasing the tube holder flanges 85 from their engagement with the slots of the retaining members 64. The specimen collection tube holder 80 may then be separated from the container lid 24. The user may also utilize the wings 86 to lift the specimen collection tube holder 80 away from the container lid 24.

While a quarter-turn connection/disconnection is disclosed herein, it is to be understood that other types of connection interfaces between the specimen collection tube holder 80 and the container lid (e.g., a bayonet connection, a snap-fit connection) are also possible.

Figure 6A:
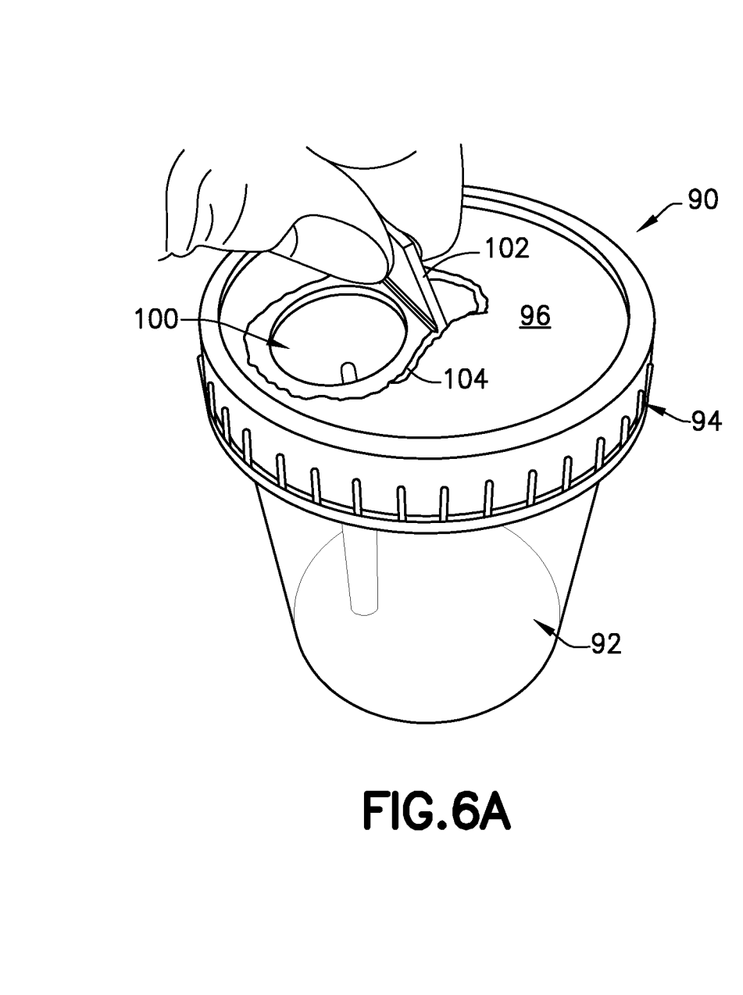
FIG. 6A is a top perspective view of a fluid sample collection container assembly in a first use configuration in accordance with another aspect of the present disclosure.
Figure 6B:
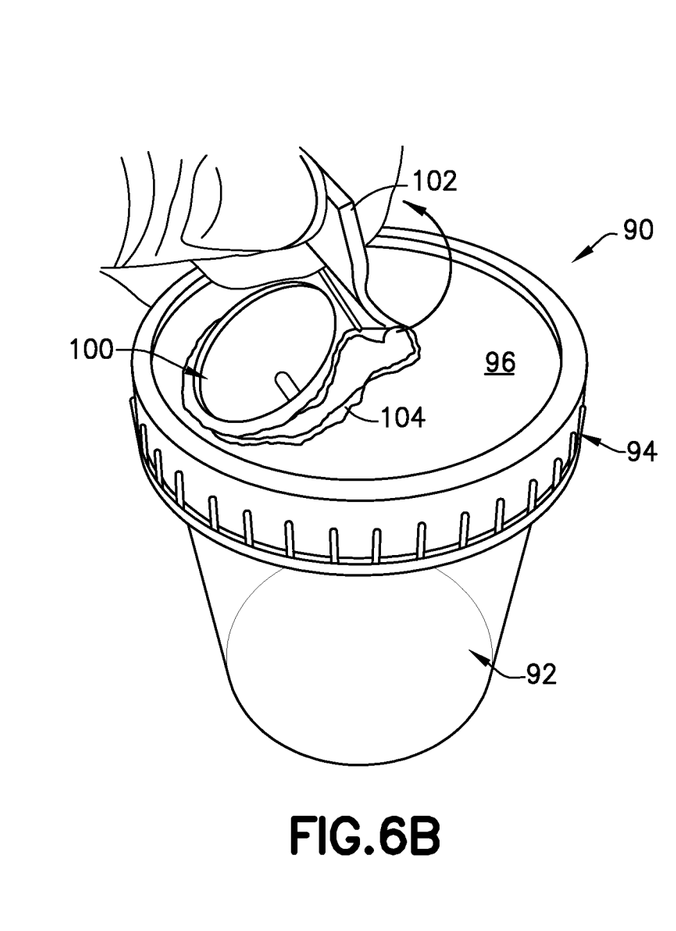
FIG. 6B is a top perspective view of the fluid sample collection container assembly of FIG. 6A in a second use configuration.

Next, referring to FIGS. 6A and 6B, a fluid sample collection container assembly 90 in accordance with another aspect of the present disclosure is shown.

Fluid sample collection container assembly 90 includes a collection container 92 and a container lid 94 removably coupled thereto. An exemplary collection container assembly 90 in accordance with the present disclosure may be used to safely collect a fluid specimen (e.g., urine), transport the fluid specimen, and draw a sample of the fluid specimen.

As opposed to fluid sample collection container assemblies 20, 70 described above with respect to FIGS. 1-5, which incorporated separate specimen collection tube holders 50, 80, respectively, container lid 94 of fluid sample collection container assembly 90 includes an initially integrated specimen collection tube holder 100. Specimen collection tube holder 100 includes a receiving cavity sized and shaped to receive a specimen collection tube such as, e.g., an evacuated tube (not shown). While not shown, a needle is disposed within the specimen collection tube holder 100, wherein the needle is configured to pierce a stopper of the specimen collection tube when the specimen collection tube is inserted into the receiving cavity. In this way, a fluid specimen within collection container 92 can be transferred to the specimen collection tube without the need to remove container lid 94.

Specimen collection tube holder 100 is coupled to a central portion 96 of container lid 94 by way of a perforated seam 104, wherein perforated seam 104 extends circumferentially around the receiving cavity of specimen collection tube holder 100. Additionally, a pull tab 102 is coupled to the specimen collection tube holder 100 and extends above the central portion 96 of container lid 94. As shown in FIG. 6B, after a user has completed all specimen sample collection via the specimen collection tube holder 100, the user (e.g., a healthcare worker) may pull upwards on pull tab 102, which tears or otherwise breaks the perforated seam 104 and separates the specimen collection tube holder 100 from the container lid 94. Once fully separated, the specimen collection tube holder 100 can be disposed of in an appropriate sharps or sharps biohazard container, while the remainder of the container lid 94 and the collection container 92 can be disposed of in a general waste container.

Figure 7:
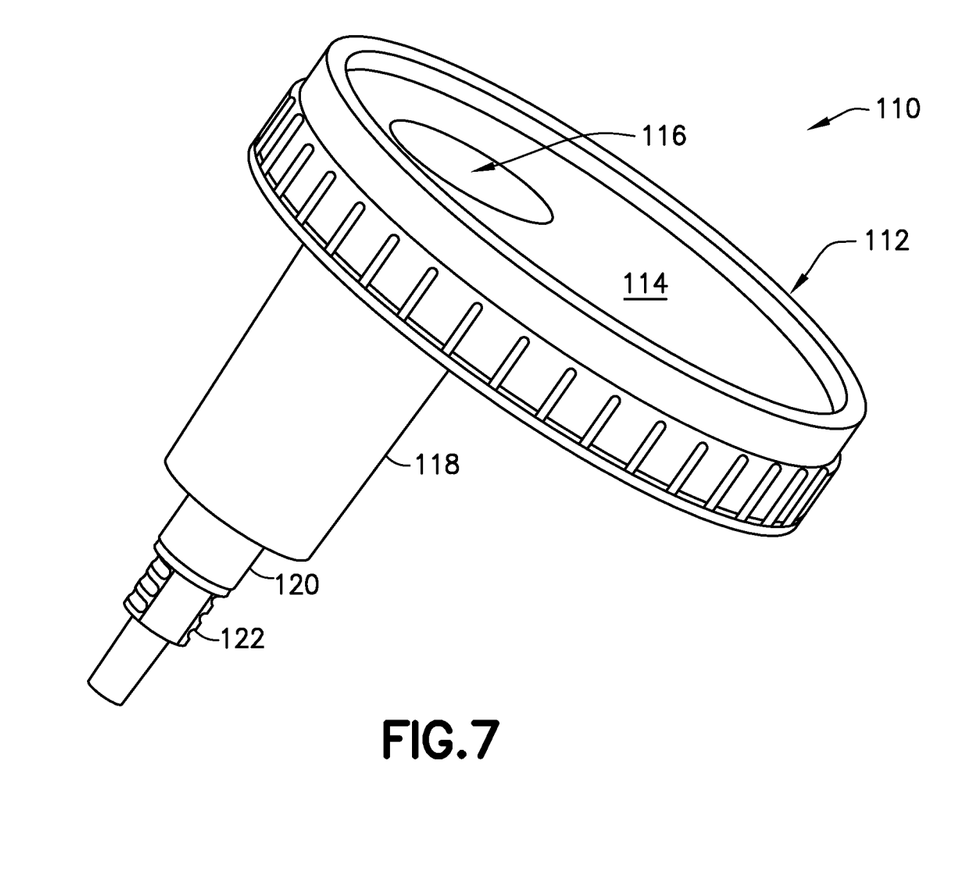
FIG. 7 is a bottom perspective view of a container lid assembly for use with a fluid sample collection container assembly in accordance with another aspect of the disclosure.

Referring now to FIG. 7, a container lid assembly 110 in accordance with another aspect of the disclosure is shown. While the fluid sample collection container assemblies described above with respect to FIGS. 1-6B each included a specimen collection tube holder separable from the respective container lids, container lid assembly 110 includes an integrated specimen collection tube holder. Specifically, container lid assembly 110 includes a container lid 112 having a central portion 114. A receiving cavity 116 is integrally formed in container lid 112, extending downward from central portion 114. The receiving cavity 116 is formed within an elongate receptacle 118, with the elongate receptacle 118 and receiving cavity 116 being sized and shaped to receive a specimen collection tube such as, e.g., an evacuated tube (not shown). While not shown, a needle is disposed within elongate receptacle 118, wherein the needle is configured to pierce a stopper of the specimen collection tube when the specimen collection tube is inserted into the receiving cavity 116. In this way, a fluid specimen can be transferred to the specimen collection tube without the need to remove container lid 112.

At a distal end of elongate receptacle 118 is a coupling interface 120, which is configured to couple to a finger grip luer adapter (FGLA) 122. One end of the FGLA 122 includes an opening configured to allow a fluid specimen to be drawn therethrough, while the other end of the FGLA 122 includes the needle described above. The FGLA 122 may be coupled to the coupling interface 120 via any appropriate connection type, such as, e.g., a threaded connection, a press-fit connection, etc.

After the user has completed all specimen collection using the container lid assembly 110, the entire container lid assembly 110 may be removed from the collection container (not shown). The user (e.g., a healthcare worker) can then separate the FGLA 122 from the elongate receptacle 118 by, e.g., rotating or pulling the FGLA 122. With the FGLA 122 separated from the remainder of the container lid 112, the FGLA 122 (with attached needle) may be disposed of in an appropriate sharps container, while the remaining container lid 112 (and collection container) can be disposed of in a general waste container. Thus, the amount of waste necessary for disposal in a sharps container is greatly reduced.

While several embodiments of a fluid sample collection container assembly are shown in the accompanying figures and described hereinabove in detail, other embodiments will be apparent to, and readily made by, those skilled in the art without departing from the scope and spirit of the invention. For example, it is to be understood that this disclosure contemplates, to the extent possible, that one or more features of any embodiment can be combined with one or more features of any other embodiment. Accordingly, the foregoing description is intended to be illustrative rather than restrictive.

What is claimed is:

1. A container assembly for collecting a fluid specimen, comprising:
    a collection container defining a chamber for receiving the fluid specimen; and
    a container lid couplable to an open end of the collection container to at least partially close the open end thereof; and
    a specimen collection tube holder at least partially internal to the collection container having an elongated receptacle formed therein and a needle, the elongated receptacle configured to receive a specimen collection tube,
    wherein the specimen collection tube holder is removably couplable to a central portion of the container lid such that at least a portion of the elongated receptacle extends into the chamber of the collection container when the container lid is coupled to the collection container and the specimen collection tube holder is coupled to the container lid,
    wherein the container lid further comprises at least one retaining member, wherein the at least one retaining member is configured to secure the specimen collection tube holder to the container lid.

2. The container assembly of claim 1, wherein the central portion of container lid comprises an opening sized and configured to receive the elongated receptacle of the specimen collection tube holder.

3. The container assembly of claim 1, wherein the specimen collection tube holder comprises at least one flange arranged peripherally to a receiving cavity of the elongated receptacle.

4. The container assembly of claim 3, wherein the at least one flange is configured to engage the at least one retaining member.

5. The container assembly of claim 4, wherein the at least one retaining member comprises a slot, and the at least one flange is configured to engage the slot when the specimen collection tube holder is coupled to the container lid.

6. The container assembly of claim 3, wherein the specimen collection tube holder further comprises a pair of opposed, upwardly extending wings arranged peripherally to the receiving cavity of the elongated receptacle.

7. The container assembly of claim 1, wherein the specimen collection tube holder is couplable to the container lid by a quarter-turn rotation in a first direction and decouplable from the container lid by a quarter-turn rotation in a second direction.

8. The container assembly of claim 1, wherein the needle is fully internal to the specimen collection tube holder.

9. A container lid assembly for use with a container assembly for collecting a fluid specimen, the container lid assembly comprising:
    a container lid configured to be couplable to an open end of a collection container; and
    a specimen collection tube holder having an elongated receptacle formed therein, the elongated receptacle configured to receive a specimen collection tube, the specimen collection tube holder coupled to the container lid by a perforated seam and comprising a pull tab, and an upward pulling force on the pull tab tearing the perforated seam and separating the specimen collection tube holder from the container lid;
    wherein the specimen collection tube holder is removably couplable to a central portion of the container lid.

10. The container lid assembly of claim 9, wherein the container lid further comprises at least one retaining member, and wherein the at least one retaining member is configured to secure the specimen collection tube holder to the container lid.

11. The container lid assembly of claim 10, wherein the specimen collection tube holder comprises at least one flange arranged peripherally to a receiving cavity of the elongated receptacle.

12. The container lid assembly of claim 11, wherein the at least one flange is configured to engage a slot formed in the at least one retaining member when the specimen collection tube holder is coupled to the container lid.

13. The container lid assembly of claim 11, wherein the specimen collection tube holder further comprises a pair of opposed, upwardly extending wings arranged peripherally to the receiving cavity of the elongated receptacle.

14. A method of forming a container assembly for collecting a fluid specimen, the method comprising:
    providing a collection container defining a chamber for receiving the fluid specimen;
    providing a container lid couplable to the collection container;
    providing a specimen collection tube holder separate from the container lid, the specimen collection tube holder having an elongated receptacle formed therein, the elongated receptacle configured to receive a specimen collection tube, the specimen collection tube holder coupled to the container lid by a perforated seam and comprising a pull tab, and an upward pulling force on the pull tab tearing the perforated seam and separating the specimen collection tube holder from the container lid; and
    coupling the specimen collection tube holder to a central portion of the container lid such that at least a portion of the elongated receptacle extends into the chamber of the collection container when the container lid is coupled to the collection container and the specimen collection tube holder is coupled to the container lid.

15. The method of claim 14, further comprising decoupling the specimen collection tube holder from the container lid when a specimen collection task is completed, and disposing of the specimen collection tube holder separately from the container lid and the collection container.

* * * * *

UNITED STATES PATENT AND TRADEMARK OFFICE
CERTIFICATE OF CORRECTION

| | | |
|---|---|---|
| PATENT NO. | : 12,318,075 B2 | Page 1 of 1 |
| APPLICATION NO. | : 18/013061 | |
| DATED | : June 3, 2025 | |
| INVENTOR(S) | : David Colie Wight et al. | |

It is certified that error appears in the above-identified patent and that said Letters Patent is hereby corrected as shown below:

In the Specification

Column 1, Line 7, delete "State, nation" and insert -- States national phase --

Signed and Sealed this
Nineteenth Day of August, 2025

Coke Morgan Stewart
*Acting Director of the United States Patent and Trademark Office*